United States Patent [19]

Marbry

[11] 4,354,491
[45] Oct. 19, 1982

[54] FLUID TRANSFER DEVICE

[76] Inventor: Steven L. Marbry, 1806 Apollo Dr., Las Cruces, N. Mex. 88001

[21] Appl. No.: 106,512

[22] Filed: Dec. 26, 1979

Related U.S. Application Data

[63] Continuation-in-part of Ser. No. 20,956, Mar. 18, 1979, abandoned, which is a continuation of Ser. No. 778,024, Mar. 15, 1977, abandoned.

[51] Int. Cl.³ ............................................. A61M 5/00
[52] U.S. Cl. ......................... 128/214.4; 128/DIG. 16
[58] Field of Search .................... 128/214.4, 221, 348, 128/DIG. 16, 214 R, 347

[56] References Cited

U.S. PATENT DOCUMENTS

| | | | |
|---|---|---|---|
| 2,829,644 | 4/1958 | Anderson | 128/221 |
| 2,842,133 | 7/1958 | Uhma | 128/214.4 X |
| 3,094,124 | 6/1963 | Birtwell | 128/348 |
| 3,472,232 | 10/1969 | Earl | 128/214.4 |
| 3,550,591 | 12/1970 | MacGregor | 128/214.4 |
| 3,570,485 | 3/1971 | Reilly | 128/214.4 |
| 3,584,625 | 6/1971 | Swick | 128/214.4 |
| 3,598,126 | 8/1971 | Hoeltzenbein | 128/348 |
| 3,603,311 | 9/1971 | Huggins | 128/214.4 |
| 3,630,198 | 12/1971 | Henkin | 128/348 X |
| 3,633,579 | 1/1972 | Alley et al. | 128/214.4 |
| 3,766,915 | 10/1973 | Rychlik | 128/214.4 |
| 3,835,863 | 9/1974 | Goldberg et al. | 128/350 R |
| 3,921,631 | 11/1975 | Thompson | 128/214.4 |

FOREIGN PATENT DOCUMENTS

| | | | |
|---|---|---|---|
| 2063484 | 6/1972 | Fed. Rep. of Germany | 128/214.4 |
| 2272691 | 12/1975 | France | 128/214.4 |
| 904237 | 8/1962 | United Kingdom | 128/214.4 |

OTHER PUBLICATIONS

Mitchell–Brit. Med. Jour.–Feb. 1952, p. 435.

Primary Examiner—Dalton L. Truluck
Attorney, Agent, or Firm—Cushman, Darby & Cushman

[57] ABSTRACT

A device for inserting a catheter tube in a vein or the like. The needle portion of the device is slotted along one position and partially along another position so that the needle after withdrawal from the body may be separated from the tube by withdrawing the tube through the continuous slot. The adapter portion of the device attached to the needle may be rigid or non-rigid. If it is rigid, it is preferably tapered toward the rear. The continuous slot may be tapered or non-tapered. A novel tapered catheter with a slot at the narrow end may be employed with the insertion device.

7 Claims, 24 Drawing Figures

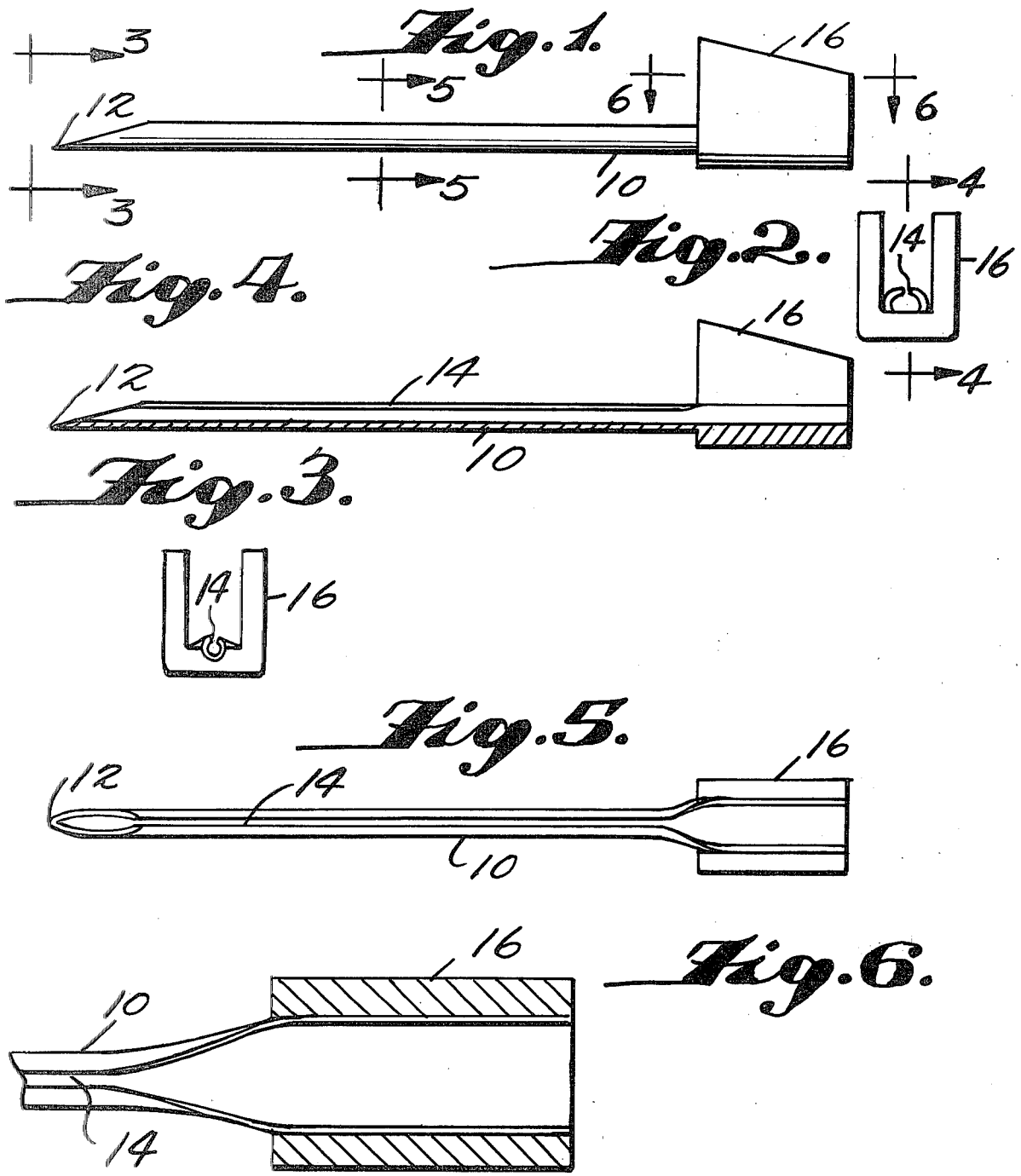

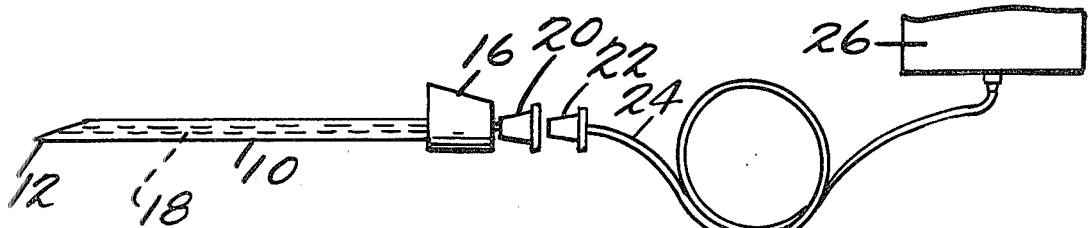
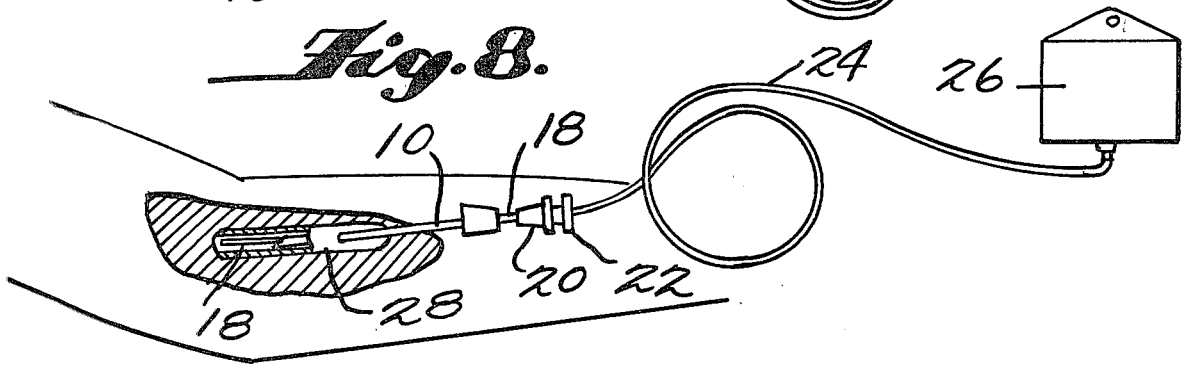
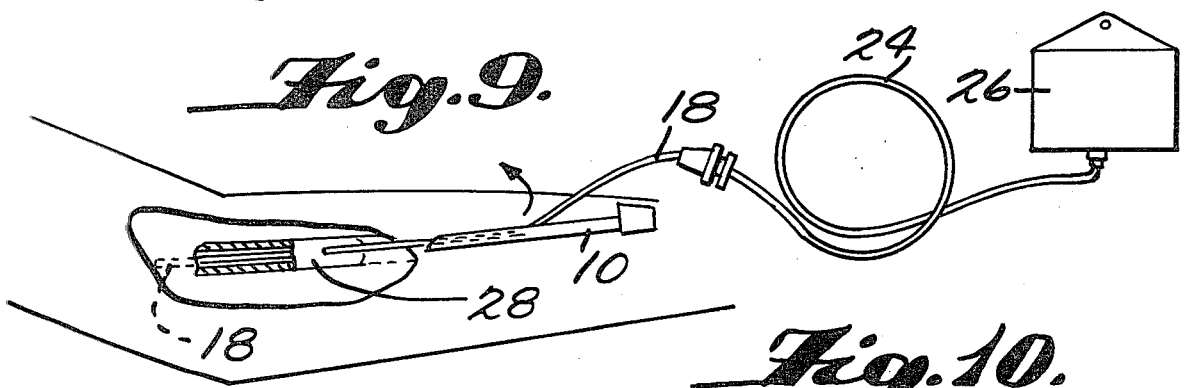
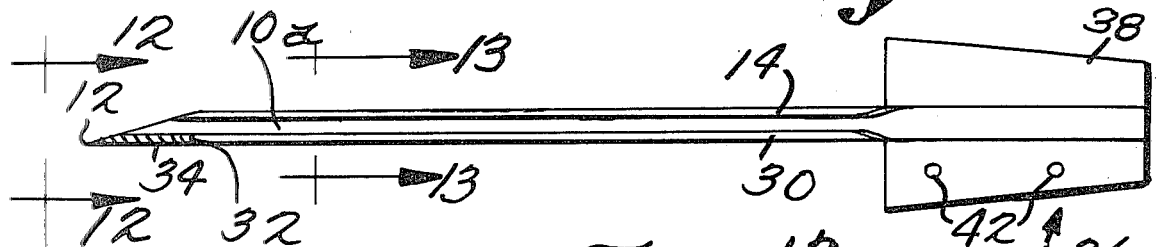
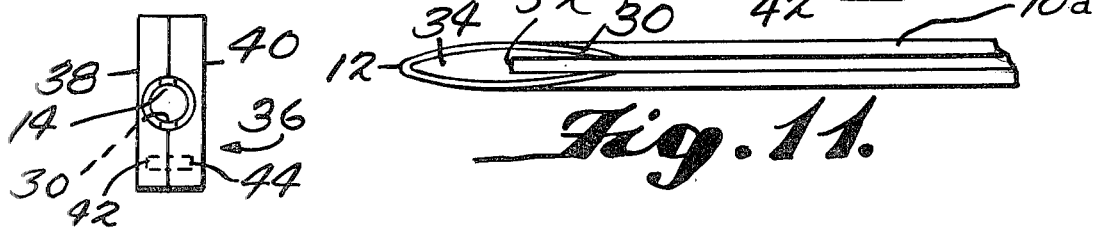

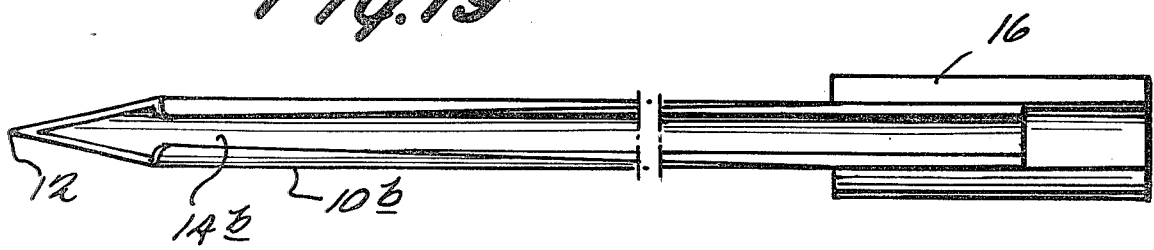
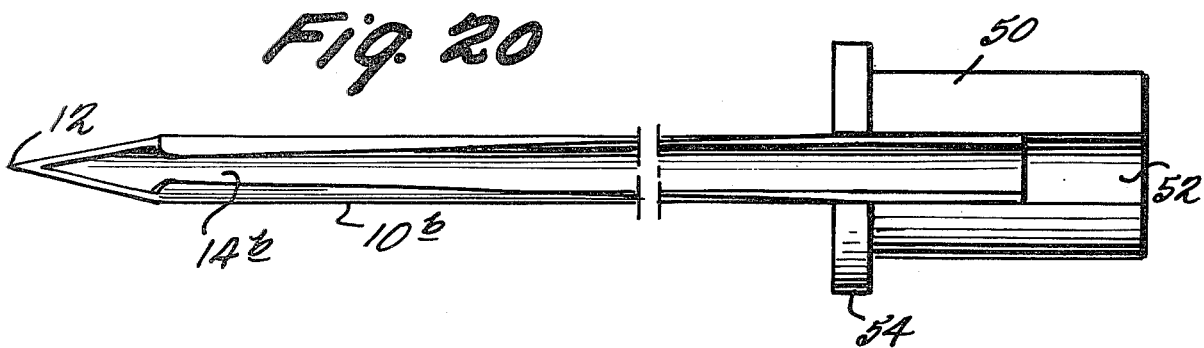
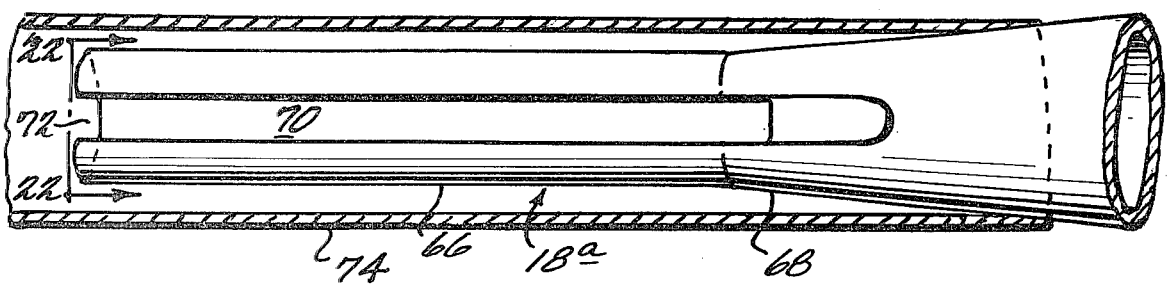
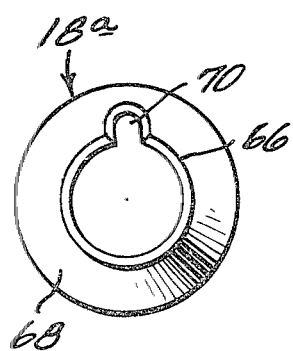

FLUID TRANSFER DEVICE

This application is a continuation-in-part application of copending application Ser. No. 20,956, filed Mar. 13, 1979, now abandoned, which is a continuation of copending application Ser. No. 778,024, filed Mar. 15, 1977, now abandoned.

This invention pertains to devices for the transfer of fluids, and in particular to the use of catheters for transfer of fluids (liquids or gases) into or from the body.

It is a well known practice to place a catheter tube into the body, e.g., into a vein, by maintaining the end of the tube within a hollow needle while the needle is inserted into the interior of the vein. The tube is then pushed through the needle until any desired length of the tube is within the vein. The needle is then withdrawn from the body while the tube is held against withdrawal. However, a serious problem exists because the needle cannot subsequently be removed from the tube. It is impossible to slide the needle off the tube at the outer end of the latter, because present intravenous (IV) tubing equipment is such that maintenance of sterility and safety factors require that the adapter utilized on the catheter tube is of a larger diameter than the inserting needle. Furthermore, the catheter tube must be fixed permanently to the adapter to prevent possible separation of the catheter tube from the adapter with movement or slippage of the catheter into the vein and resultant passage of the catheter to other internal parts of the body.

To overcome this problem, a slot has been provided along the entire length of the needle at a position of the wall generally opposite from the leading or cutting edge of the needle. U.S. Pat. No. 3,603,311 to Huggins (1971), U.S. Pat. No. 3,550,591 to MacGregor (1970), U.S. Pat. No. 3,584,625 to Swick (1971), U.S. Pat. No. 3,472,232 to Earl (1967), U.S. Pat. No. 2,842,133 to Uhma (1958), U.S. Pat. No. 2,829,644 to Anderson (1958), British Pat. No. 904,237 to Elliott (1962), German Reference No. 2,055,027 (1971) and German Reference No. 2,063,484 (1972) and an article by Mitchell in *The British Medical Journal*, February, 1952, page 435, all teach a needle with some form of slot.

After the insertion is made and the catheter tube is positioned within the body, the needle is withdrawn from the body. The needle and catheter tube are then separated from each other by slipping the tube through the slot in the needle.

However, a number of problems still remain with these prior art devices. Specifically, due to the shape of the needle, it is extremely difficult to maintain the sterile field about the insertion site. In many instances, surgical draping of the insertion site is necessary to guard against contamination of the catheter during placement.

This fact, plus the complexity of a number of the prior art needles make their use difficult and slow. Also, the complexity increases the manufacturing costs of these needles.

Furthermore, in some of the prior art needles, the resistance between the needle and catheter makes difficult the removal of the catheter after insertion. If undue force is necessary to remove the catheter, the possibility of completely pulling the catheter out of the insertion site increases.

The present invention overcomes these problems. In the present invention, a needle having a continuous slot is provided with an adapter on the end of the needle opposite the cutting or leading edge. The height of the adapter is continuously tapered from a greatest height near the needle to the least height away from the needle. This enables the use of any of the three or four catheter guards currently on the market which have varying diameters so that sterility around the insertion site is easily maintained.

In an alternative embodiment, the adapter is not tapered, but is made of a non-rigid material. The use of a non-rigid material enables a tight fit between the adapter and the catheter guard so that the sterile field is easily maintained. Furthermore, the non-rigid adapter also increases the ease of catheter insertion. The position of the catheter with respect to the insertion needle may be fixed by squeezing the adapter. When the needle is to be removed, less pressure is applied to the adapter so that the needle can slip with respect to the catheter.

In addition, a further embodiment of the invention employs a tapered slot in the needle. The tapered slot enables a smooth removal of the catheter from the needle and minimizes the possibility of detrimental tension or pulling on the catheter.

The inventor has also developed a novel catheter useful with "through the needle" type insertion devices which is tapered and has a slot at the narrow end.

These and other objects and advantages of the invention will become more apparent and more readily appreciated from the following detailed description of the presently preferred exemplary embodiments of the invention taken in conjunction with the accompanying drawings, of which:

FIG. 1 is a side view of a needle having a rigid adapter in accordance with the invention;

FIG. 2 is a right hand end view of the needle of FIG. 1;

FIG. 3 is a left hand end view of the needle of FIG. 1;

FIG. 4 is a cross-sectional view taken along line 4—4 of FIG. 2;

FIG. 5 is a top view of FIG. 1;

FIG. 6 is a cross-sectional view taken along the line 6—6 of FIG. 1;

FIG. 7 shows a catheter tube in place in the needle and ready for connection to a supply of fluid to be transferred;

FIG. 8 shows the needle in place in a vein and the catheter tube pushed into the vein beyond the end of the needle;

FIG. 9 shows the catheter tube being separated from the needle after withdrawal of the needle from the vein;

FIG. 10 is a cross-sectional view taken along a symmetrical vertical plane of a needle having two slots in accordance with the invention;

FIG. 11 is a top view of the cutting end of the needle of FIG. 10;

FIG. 12 is a left hand end view taken at line 12—12 of FIG. 10;

FIG. 13 is a cross section at line 13—13 of FIG. 13;

FIG. 19 is a top view of the needle in FIG. 1, except with a tapered slot;

FIG. 20 is a top view of the needle in FIG. 14, except with a tapered slot;

FIG. 21 is a top view of a catheter;

FIG. 22 is an end view taken along the 22—22 line of FIG. 21;

Figure 14:
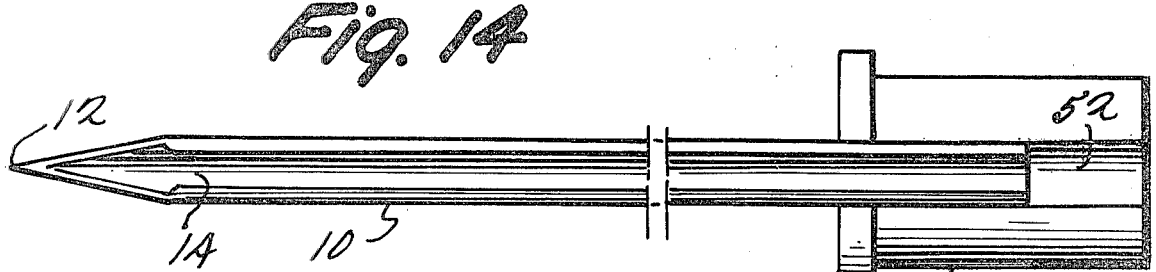
FIG. 14 is a top plan view of a needle having a non-rigid adapter in accordance with the invention.

In FIGS. 1-9 of the drawing, hollow needle 10 has a cutting edge terminating at forward tip 12. Continuous slot 14, in the needle wall, is positioned opposite from the position of the cutting edge 12. At the end of the needle opposite tip 12 tapered adapter 16, which is U-shaped in cross section, is provided for facilitating a grip on the needle for insertion thereof into and withdrawal from a vein, as described below. As is evident from the FIGS. 1 and 2, adapter 16 has its greatest height near needle 10 and decreases with increasing to its least height on the opposite end. Needle 10 may be affixed to adapter 16 in any convenient manner, for example, by laying the end of the needle open as best shown in FIGS. 4, 5 and 6 to fit the inner bottom contour of adapter 16, and welding the two parts together.

The taper of adapter 16 provides a very useful and advantageous function. As is well known in the art, a catheter guard sleeve usually is attached to the needle, or more precisely, to the adapter therefore, in order to maintain the sterile field about the portion of the catheter that will be inserted within the patient. There are three or four catheter guards currently on the market, each having different diameters. The taper of adapter 16 enables any of these sleeves to be used with the present invention.

FIG. 7 shows needle 10 with catheter tube 18 inside the needle. Tube 18 has an outer diameter less than the inner diameter of the needle so that it is freely slidable thereon. Slot 14 has a lesser width than the outer diameter of tube 18, but the thickness of the wall of the needle and the width of the slot should be selected so that with modest force the wall of the needle and/or the tube will yield and the tube may be stripped out of the needle through the slot. In FIG. 7, tube 18 is fitted with hollow receptacle 20 at its outer end. Hollow plug 22 is attached to a further tube 24 which extends to a so-called IV bottle 26. When plug 22 is inserted into receptacle 20 fluid may pass through tubes 18 and 24 as desired.

In use, the needle is inserted into vein 28 to a position as shown in FIG. 8. Catheter tube 18, which is shown connected to the fluid supply container 26, is pushed through the needle until the end of the tube is a desired distance into the vein, as shown in FIG. 8. The needle is then withdrawn from the body, to a position such as that shown in FIG. 9. The needle is separated from the tube by pulling the tube through the slot 14. In this way the needle may be removed from the tube with or without disconnecting the tube 18 from the tube 24 leading to the fluid supply apparatus.

A modification of the invention is shown in FIGS. 10-13. Here the needle, designated 10a, has slot 14 and an additional slot 30. Slot 30 is located opposite from slot 14, dividing the needle into two parts, except near the cutting edge 12. Slot 30 terminates at point 32, leaving a web of needle material 34 for holding the two parts of the needle together at the incision end. Modified adapter 36 is fitted to needle 10a, being comprised of two side-by-side plates 38 and 40, each fastened to one side of the tube 10a. Adapter 36 is tapered as illustrated in FIG. 10 and as described above with respect to adapter 16 for the reasons discussed above. The plates have mating recesses at 38a and 40a to provide a passage for tube 18. However, plates 38 and 40 are not connected to each other. Therefore, when catheter tube 18 is to be withdrawn from needle 10a through slot 14, plates 38 and 40 may be moved apart sufficiently for tube 18 to pass therebetween. The needle sides are sufficiently flexible to permit this separation of the plates. If desired, plate 38 may have apertures 42 therein, into which pins 44 fixed in plate 40 would be inserted for indexing purposes.

The needle of FIGS. 10-13 has the advantage of separation of the needle parts, except at the cutting end, to thereby facilitate the separation of catheter tube 18 from the needle.

The fact that slot 30 does not intercept cutting edge 12 of the needle means that a complete incision is made through the wall of the vein, without leaving any segment of vein wall to impede the movement of the catheter tube through the needle. The present design thusly avoids the formation of a tissue plug on incision of the skin and vein. The present inventor has discovered that the incision a needle makes in a venipuncture is actually related to the transverse diameter of the needle rather than its circumference. Therefore, open slot 14 in the needle at a position opposite the cutting edge does not present any problems of the type just mentioned.

Figure 15:
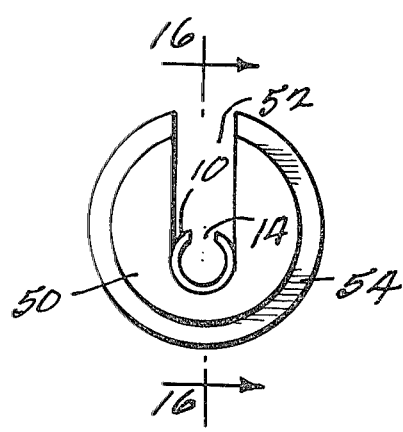
FIG. 15 is an end elevation view of FIG. 14.
Figure 16:
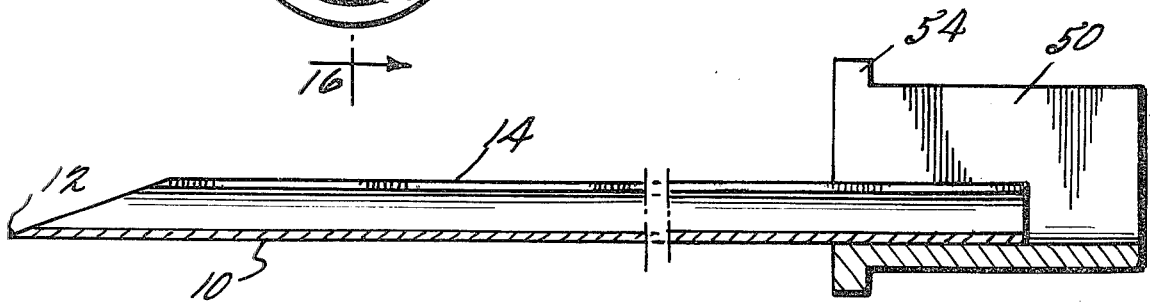
FIG. 16 is a cross-sectional view taken along the 16—16 line of FIG. 15.

A further modification of the invention is shown in FIGS. 14-16. In this embodiment, needle 10 has slot 14 as discussed with respect to FIGS. 1-9. Adapter 50, which is not tapered as is the adapter in the embodiments illustrated in FIGS. 1-13, is attached to the needle. However, adapter 50 is made of a non-rigid material. In the preferred embodiment, adapter 50 is a non-rigid plastic. Adapter 50 is cylindrical with slot 52 cutting longitudinally, partially therethrough. Annulus 54 is provided on adapter 50 to facilitate the gripping of adapter 50 and insertion of catheter 18. As illustrated in FIG. 15, slot 52 aligns with slot 14. During insertion, catheter 18 lies along the hollow portion of needle 10 and at the bottom of slot 52. Although adapter 50 is illustrated as non-tapered, it can also be tapered.

Adapter 50 greatly simplifies the maintenance of sterility of the entire needle-catheter assembly during placement of the catheter into a vein or other lumen. The use of a non-rigid adapter enables a tight fit between adapter 50 and the catheter guard. This tight fit, in addition to the passage of the catheter through deep U-shaped slot 52 serves to function operatively so that the catheter placement can be done quickly, conveniently and aseptically.

Non-rigid adapter 50 also enables control of the position of catheter 18 passing therethrough during insertion. This enables the maintenance of sterility of the unit and proper placement of the catheter in the vein.

Figure 17:
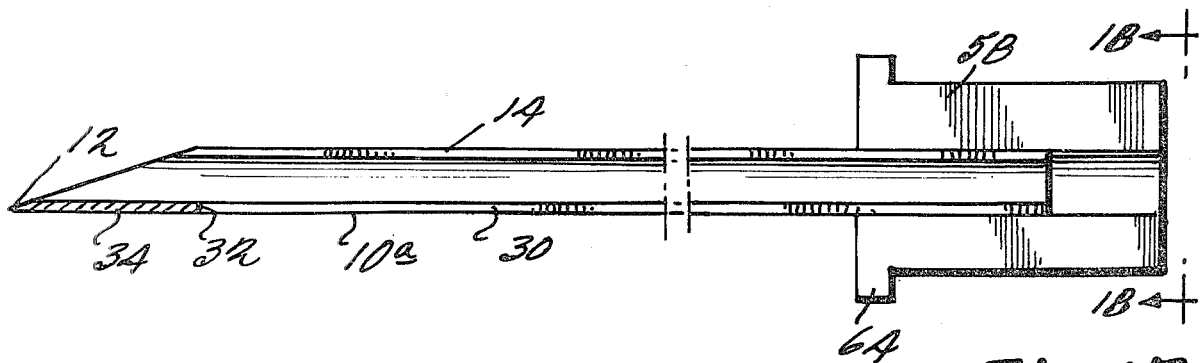
FIG. 17 is a cross-sectional view taken along a symmetrical vertical plane of a needle having a non-rigid adapter and two slots in accordance with the invention.
Figure 18:
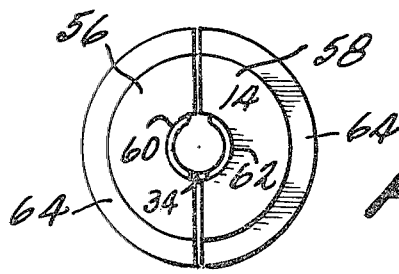
FIG. 18 is an end view taken along the 18—18 line of FIG. 17.

FIGS. 17 and 18 illustrate another embodiment of the present invention with a needle 10a similar to the needle in FIGS. 10-13 attached to adapter portions 56 and 58. As discussed above with respect to FIGS. 10-13, needle 10a comprises slots 14 and 30 on opposite sides of the needle body. Slot 14 extends the entire length of the needle, while slot 30 stops at point 32 to leave web 34 connecting the needle halves. Each half of needle 10a is connected to adapter portions 56 and 58, respectively. These portions are made of a non-rigid material, preferably non-rigid plastic. Grooves 60 and 62 are provided in adapter portions 56 and 58, respectively, to permit passage of the catheter through the adapter portions and the hollow portion of needle 10a. Annular portions 64 on adapter portions 56 and 58 facilitate grasping the adapter portions during insertion and withdrawal of needle 10a. All of the advantages discussed above with respect to the inclusion of slot 30 and a non-rigid adapter accrue to this embodiment of the present invention.

FIGS. 19 and 20 illustrate a variation on the embodiments illustrated in FIGS. 1–9 and 14–16, respectively. In the embodiments illustrated in FIGS. 19 and 20, needles 10b have slots 14b which are tapered, instead of uniform as illustrated in FIGS. 1–9 and 14–16. The narrowest portion of slot 14b is near cutting edge 12, and the slot tapers continuously to nearly the opposite end of the needle. The precise width of the slot of the needle can be varied depending on the specific use of the needle and the size and shape of the catheter with which it is to be used. In the preferred embodiment, the minimum width of the slot near cutting edge 12 is approximately 0.01 mm less than the outer diameter of catheter 18. The slot then gradually widens toward the opposite end to a width approximately equal to the outer diameter of the needle. The use of a tapered slot greatly increases the ease of removal of the needle from either the standard intravenous catheter presently in use, or tapered and various other shaped catheters.

The conventional wisdom of prior art needle-makers is that the entire length of the slot in the needle must be made as narrow as possible. This results from a belief that a narrower slot increases the ease of venipuncture and decreases the discomfort experienced by the patient. However, the present inventor has discovered that this is not accurate. As indicated above, the incision a needle makes in a venipuncture is actually related to the transverse diameter of the needle rather than its circumference.

This discovery enables the employment of a wider flared slot in the needle which results in a number of distinct advantages over narrow slotted needles. A needle with a wider flared slot is much simpler and easier to use in actual practice. Furthermore, the use of a wider flared slot greatly increases the versatility of the needle, allowing use with more types, sizes, and shapes of catheters or other devices. In addition, the needle with the wider flared slot is much easier and more economical to manufacture than prior art devices.

One of the major problems with "through the needle" catheter insertion devices is their tendency to leak around the venipuncture site. The outer diameter of the standard intravenous catheter must obviously be less than the outer diameter of the needle, and accordingly the resulting venipuncture hole is always of a larger diameter than the cathether.

FIGS. 21 and 22 illustrate a tapered catheter which overcomes these problems. Catheter 18a comprises a narrow, non-tapered portion 66 and tapered portion 68. Slot 70 extends from end 72 of catheter 18a well into tapered portion 68 of catheter 18a. In the preferred embodiment slot 70 extends from end 72 to a point on tapered portion 68 which has a diameter of approximately twice that of non-tapered portion 66.

Since the diameter of tapered portion 68 at the end of slot 70 is twice that of non-tapered portion 66 (which is typically the size of a conventional non-tapered catheter), slot 70 approximately doubles the effective diameter of the catheter after insertion. The volume of fluid delivered by any intravenous catheter is related to the diameter of the catheter. Thus, by effectively doubling the catheter diameter, the volume of fluid delivered increases.

Following placement of catheter 18a in vein 74 or other site, and removal of the needle, catheter 18a is advanced into vein 74 to the point where the diameter of tapered portion 68 fully occupies the opening of the venipuncture site. This maneuver, combined with proper dressing of the site and associated infusion equipment, effectively seals the skin and venipuncture site precluding any leakage of body or intravenous fluid. Further, the absence of leakage around the site also facilitates the maintenance of an aseptic environment around the catheter and related equipment, thereby decreasing the incidence of local phlebitis and other complications of present day intravenous therapy.

Figure 23:
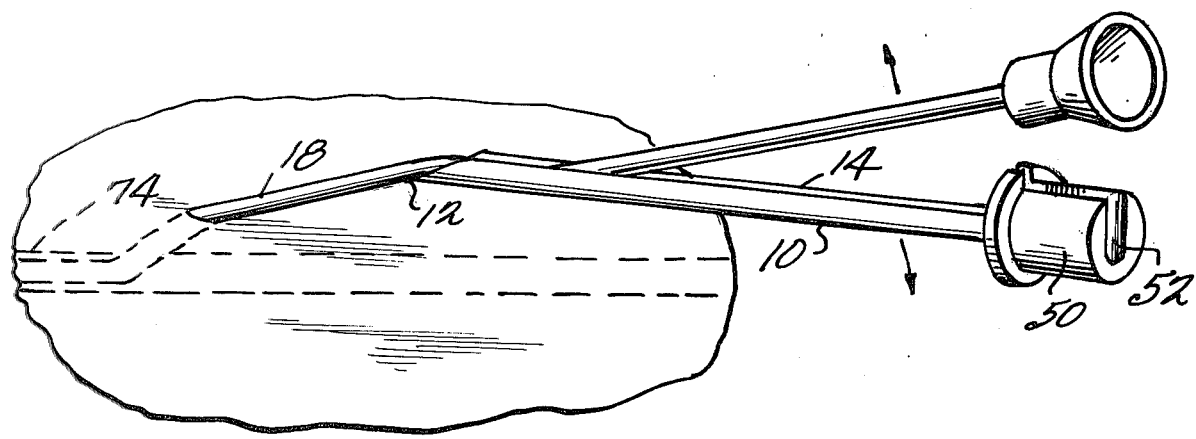
FIG. 23 illustrates schematically one method of removing the catheter from a needle in accordance with the invention.
Figure 24:
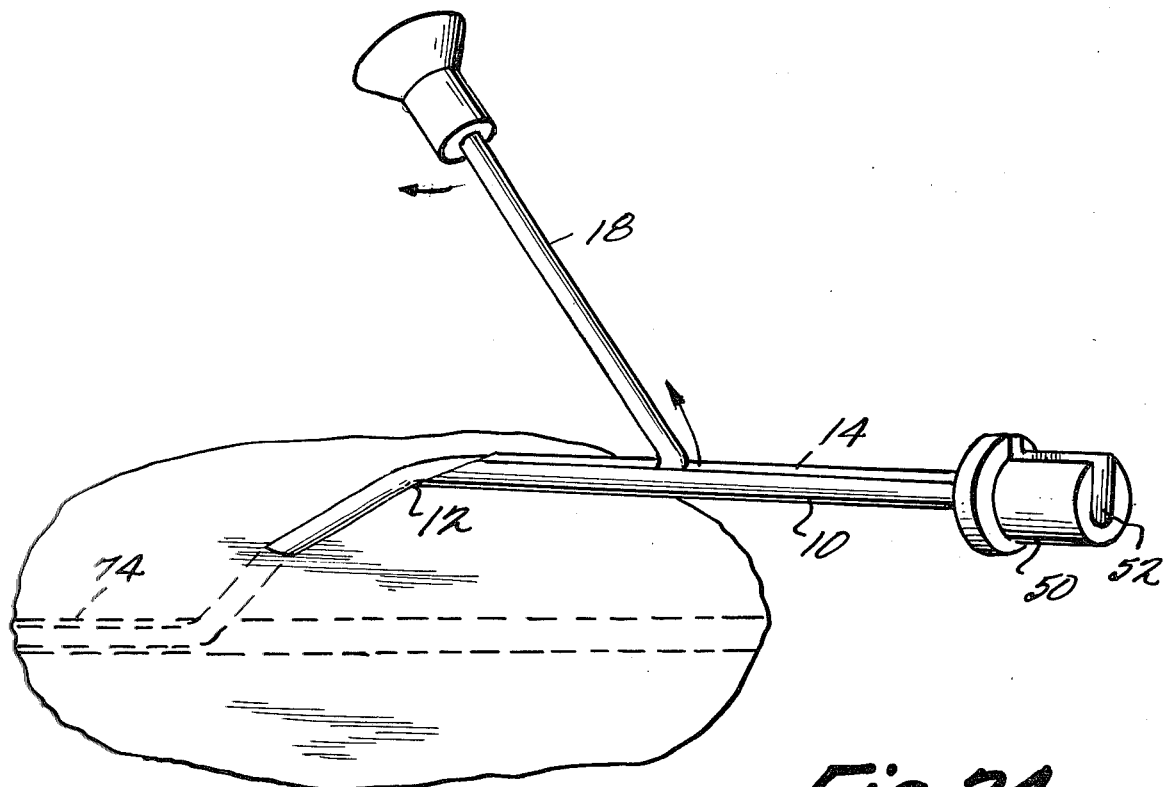
FIG. 24 illustrates a second method of removing the catheter from a needle in accordance with the invention.

FIGS. 23 and 24 illustrate two ways of removing the catheter from the needle after insertion. In the stripping method illustrated in FIG. 23, catheter 18 is pulled up and out of needle 10 through slot 14, so that the entire length of catheter 18 pulls through slot 14. At the same time, needle 10 is pulled slightly down and back. Considerable care must be taken to avoid pulling the catheter 18 out vein 74 and thus ruining the insertion procedure.

In the slipping method illustrated in FIG. 24, needle 10 is held stationary while the portion of catheter 18 in slot 52 is raised out of slot 52 until the catheter forms an angle of approximately 90° with needle 10. Forward pressure is then applied on catheter 18. The catheter then slips easily along slot 14 and out the pointed end of needle 10. Thus, only one point of catheter 18 pulls through slot 14. Since only forward pressure is applied to the catheter and the catheter moves only in the forward direction, the possibility of pulling catheter 18 out of vein 74 is avoided.

The methods of removal illustrated in FIGS. 23 and 24 are discussed with respect to the embodiment of the present invention illustrated in FIGS. 14–16. Obviously, these methods of removal apply equally to any insertion needle having a single slot, with either a tapered or non-tapered catheter, tapered or non-tapered slot, and either a rigid or non-rigid adapter.

The foregoing description has been made only for purposes of illustration, and the true scope of the invention is to be taken from the appended claim.

What is claimed is:

1. A device for supporting a fluid transfer tube, the device comprising:
    an elongated hollow needle having a first end shaped to form a cutting edge for making an incision into tissue and a second end opposite said first end;
    a slot along the length of said needle at a position in the wall thereof removed from the position of the forward extremity of the cutting edge; and
    adapter means attached to said needle for gripping and moving said needle during insertion and removal, said adapter means being generally cylindrical and defining a passage extending longitudinally from one end of said cylinder to the other, said passage having a U-shaped cross section and being aligned with the hollow portion of said needle, said needle being attached to the walls defining said passage, the smallest width of said passage being no smaller than the inner diameter of said needle, said adapter means being sufficiently non-rigid to deform upon manual squeezing of the portion of said adapter means adjacent the curved bottom portion of said U-shaped cross-section to hold a catheter passing through said passage;

the arrangement being such that the fluid transfer tube positioned within the needle may be removed from the needle through said slot therein.

2. A device for supporting a fluid transfer tube, the device comprising:

an elongated hollow needle having a first end shaped to form a cutting edge for making an incision into tissue and a second end opposite said first end;

a first slot along the length of said needle at a position in the wall thereof removed from the position of the forward extremity of the cutting edge;

a second slot in said needle wall at a position substantially opposite from said first slot, the second slot extending from said needle second end to a point adjacent to but not through said needle cutting edge; and adapter means for gripping said needle during the insertion and removal thereof, said adapter means comprising first and second portions each having an indentation, said portions forming a cylindrical body and said indentations defining a passage extending longitudinally from one end of said body to the other when said first and second portions are disposed proximately, said needle being attached to the walls defining said passage, said adapter means being sufficiently non-rigid to deform upon manual squeezing to hold in place a catheter passing through said passage;

the arrangement being such that a fluid transfer tube positioned within said needle may be removed from the needle through said first slot therein.

3. A system for administering a fluid to the body comprising:

an elongated hollow needle having a first end shaped to form a cutting edge for making an incision into tissue and a second end opposite said first end;

a slot along the length of said needle at a position in the wall thereof removed from the position of the forward extremity of the cutting edge;

adapter means for gripping and moving said needle during insertion and removal;

a catheter having a tapered portion, said catheter defining a slot extending longitudinally from one end to at least said tapered portion; and means for supplying said fluid to said catheter, the arrangement being such that said catheter within the hollow portion of said needle may be removed from said needle through said slot therein.

4. A device for inserting a fluid transfer tube, the device comprising:

an elongated hollow needle having a first end shaped to form a cutting edge for making an incision into tissue and a second end opposite said first end;

a slot along the length of said needle at a position in the wall thereof removed from the position of the forward extremity of the cutting edge, said slot being continuously tapered from a most narrow point near said needle first end and a widest point at said needle second end; and adapter means for gripping and moving said needle during insertion and removal;

the arrangement being such that a fluid transfer tube positioned within the needle may be removed from the needle through the slot therein.

5. A device for supporting a fluid transfer tube, the device comprising:

an elongated hollow needle having a first end form a cutting edge for making an incision into tissue and a second end opposite said first end;

a first slot along the length of said needle at a position in the wall thereof removed from the position of the forward extremity of the cutting edge;

a second slot in said needle wall at a position substantially opposite from said first slot, said second slot extending from said needle second end to a point adjacent to but not through said needle cutting edge, at least one of said first and second slots being continuously tapered from a most narrow point near said needle first end to a most wide point near said needle second end; and adapter means having a first end attached to said needle second end and a second end opposite said adapter means first end, for gripping said needle during the insertion and removal thereof, said adapter means comprising mating plates fastened to the respective sides of said needle defined by said first and second slots, the arrangement being such that a fluid transfer tube positioned within said needle may be removed from the needle through the slot therein.

6. A system as in claim 3, 4 or 5 wherein said adapter means having a first end attached to said needle second end and a second end, said adapter means having a greatest height at said adapter means first end, said height decreasing without increasing to the least height of said adapter means at said adapter means second end.

7. A system as in claim 3, 4 or 5 wherein said adapter means having a U-shaped cross section defining a passage aligned with the hollow portion of said needle, the smallest diameter of said passage being no smaller than the inner diameter of said needle, said adapter means being sufficiently non-rigid to deform upon manual squeezing of the portion of said adapter means adjacent the curved bottom portion of said U-shaped cross section to hold a catheter passing through said passage.

* * * * *